United States Patent [19]

Klaveness et al.

[11] Patent Number: 5,569,449
[45] Date of Patent: Oct. 29, 1996

[54] GASEOUS MICROPARTICLES AS ULTRASOUND CONTRAST AGENTS

[75] Inventors: Jo Klaveness, Oslo; Pål Rongved, Nesoddtangen; Per Strande, Oslo, all of Norway

[73] Assignee: Nycomed Imaging AS, Oslo, Norway

[21] Appl. No.: 462,401

[22] Filed: Jun. 5, 1995

Related U.S. Application Data

[62] Division of Ser. No. 146,115, Dec. 23, 1993.

[30] Foreign Application Priority Data

| Jun. 3, 1991 | [GB] | United Kingdom | 9111890 |
| Jul. 5, 1991 | [GB] | United Kingdom | 9114570 |
| Jan. 9, 1992 | [GB] | United Kingdom | 9200409 |
| Jun. 3, 1992 | [WO] | WIPO | PCT/EP92/01327 |

[51] Int. Cl.$^6$ .................................................. A61K 49/00
[52] U.S. Cl. ........................................ 424/9.51; 424/9.52
[58] Field of Search .................................. 424/9.52, 9.51

[56] References Cited

U.S. PATENT DOCUMENTS

4,985,233  1/1991  Klaveness .................................. 424/9

FOREIGN PATENT DOCUMENTS

0160266  11/1985  European Pat. Off. .

*Primary Examiner*—Brian M. Burn
*Assistant Examiner*—Mary C. Cebulak
*Attorney, Agent, or Firm*—Bacon & Thomas

[57] ABSTRACT

This invention relates to ultrasound contrast agents in the form of microparticles comprising a biotolerable matrix (e.g. of a carbohydrate or an X-ray contrast agent) in association with a gas or a precursor therefor. The contrast agents are stabilized to enhance their in vivo stability and/or echogenicity by covalently modifying the structure of the matrix, e.g. to introduce crosslinking groups or to attach lipophilic groups and/or molecules. The covalent moieties may include biodegradable linkages to assist rapid subsequent elimination of the contrast agents from the system.

13 Claims, 1 Drawing Sheet

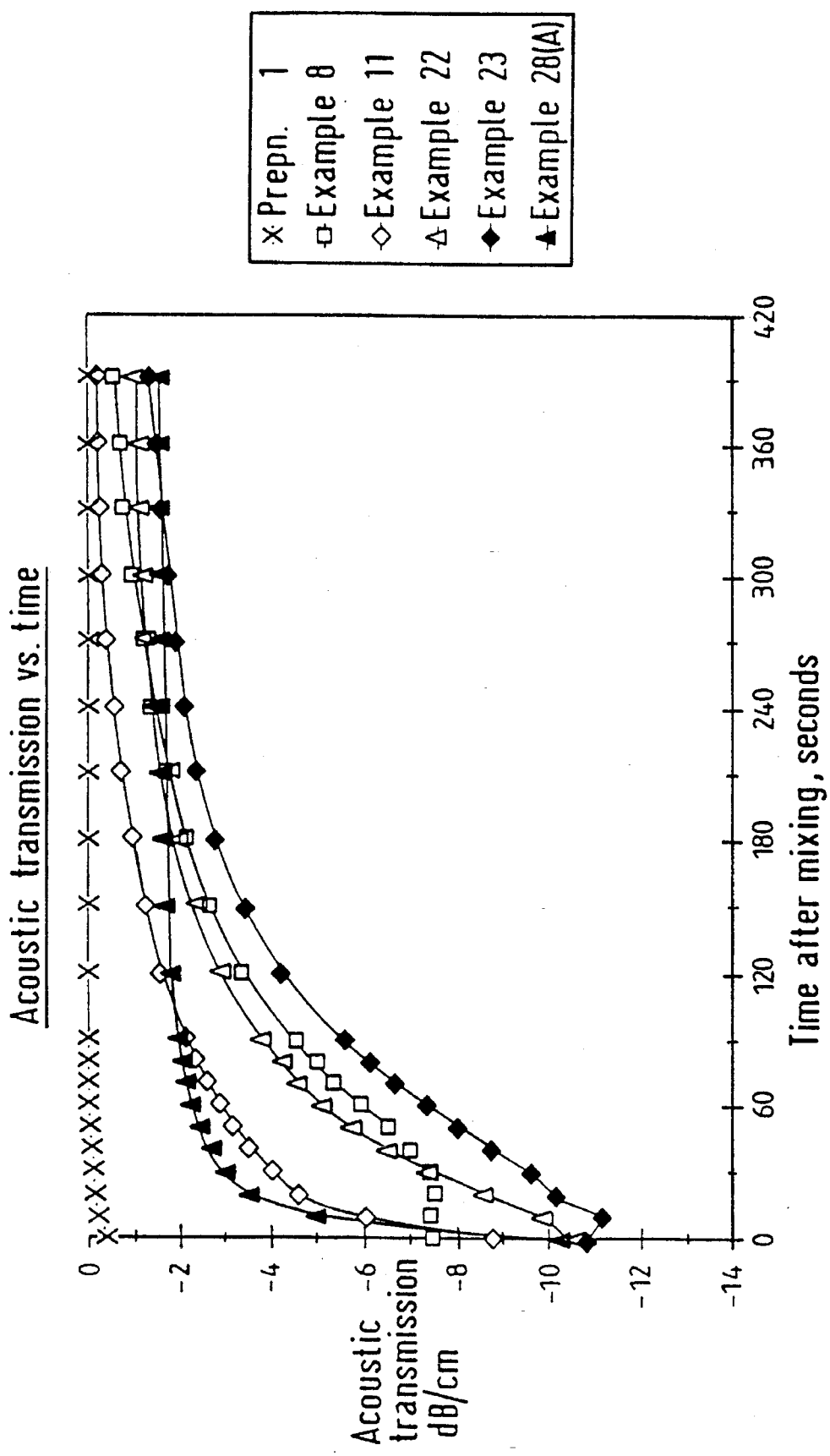

GASEOUS MICROPARTICLES AS ULTRASOUND CONTRAST AGENTS

This application is a division of application Ser. No. 08/146,115, filed Dec. 23, 1993.

This invention relates to novel contrast agents, more particularly to new microparticulate contrast agents of use in diagnostic ultrasonic imaging.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas microbubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Initial studies involving free gas microbubbles generated in vivo by intracardiac injection of physiologically acceptable substances have demonstrated the potential efficiency of such bubbles as contrast agents in echocardiography; such techniques are severely limited in practice, however, by the short lifetime of the free bubbles. Interest has accordingly been shown in methods of generating and/or stabilising gas microbubbles for echocardiography and other ultrasonic studies, for example using emulsifiers, oils, thickeners or sugars.

Techniques involving the use of sugars in ultrasound contrast agents are described in, for example, U.S. Pat. No. 4,681,119, U.S. Pat. No. 4,442,843 and U.S. Pat. No. 4,657,756, which disclose the use of particulate solids having a plurality of gas-filled voids and preferably also a plurality of nuclei for microbubble formation. EP-A-0322350, WO 88/03388, EP-A-0123235, EP-A-0122624 and DE-A-3834705 suggest ultrasound contrast agents consisting of fatty acid-coated, gas-containing microparticles which may include sugars such as cyclodextrins, monosaccharides, disaccharides or trisaccharides. U.S. Pat. No. 4,832,941 claims ultrasound contrast agents consisting of a mixture of three components: (1) macromolecules such as polysaccharides, (2) vegetable oil and (3) soluble iron (III) salts. EP-A-0077752 suggests ultrasound contrast agents consisting of gas bubbles, surface active compounds (including fatty acid salts and derivatives) and viscosity increasing substances (including mono- or polysaccharides). EP-A-0327490 describes gas-containing amylose particles coated with polymers.

Schlief, R. in *International Symposium on Contrast Media, Tokyo* (1988), pp. 323–328 gives an overview of ultrasound contrast media with focus on SHU 454 (Echovist ®), which is a saccharide-based product under development by Schering AG. The same author in *Contrast Media from past to the Future, symp. Berlin* (1987), pp. 179–187 describes SHU 454 further. Loughery, E. J. et al. in *Echocardiography* (Elsevier) (1990), pp. 279–292 have published a review on study of circulation by myocardial contrast echocardiography with focus on SHU 454, SHU 508 (Levovist ®) and the protein-based Albunex ®

Schlief, R. in *Radiology* (1991) 178, pp. 213–215 has described clinical use of SHU 454 in hysterosalpingocontrast sonography of the uterus and fallopian tubes. SHU 454 has also been described in the following publications: Rovai, D. et al., *Circulation Supplement III* (1990) 82, p. 26; Barzilai, B. et al., *Circulation Supplement III* (1990) 82, p. 96; Vorwerk, D. et al., *Ultraschall in Med.* (1990) 11, pp. 146–149; Von Bibra, H. et al., *Eur. Heart J.* (1990) 11, p. s 112; Wilkenshoff, U. et al., *Eur. Heart J.* (1990) 11, p. s 113; El Mouaaouy, A. et al., *Surg. Endosc.* (1990) 4, pp. 114–117; Smith M. D. et al., *JACC* (1984) 3, pp. 992–998; Lange, L. et al., *Arneim.-Forsch./Drug Res.* (1986) 36(II), pp. 1037–1040; Fritzsch, Th. et al., *Invest. Radiol.* (1988) 23 (Suppl 1), pp. 302–305; Arisawa, J. et al., *International Symposium on Contrast Media, Tokyo* (1988), pp. 331–332; Rovai, D. et al., *JACC* (1987) 10, pp. 125–134: Heidelmeyer, C. F. et al., *J. Cardiothoracic Anesthesia* (1990) 4, pp. 60–67; Grube, E. et al., *Z Kardiol.* (1986) 75, pp. 335–362; Meyer-Schwickerath et al., *Ultraschall* (1986) 7, pp. 34–36; and Becher, H. et al., *Am. J. Cardiol.* (1989) 64, pp. 374–377.

SHU 508 has been described in the following publications:

Schlief, R. et al., *Circulation Supplement III* (1990) 82, p. 28; Schartl, M. et al., *Circulation Supplement III* (1990) 82, p. 261; Fritzsch, T. et al., *Invest. Radiol.* (1990) 25 (Suppl), pp. 160–161; Schlief, R. et al., *Echocardiography* (1990) 7, pp. 61–64; and Smith, M. D. et al., *JACC* (1989) 13, pp. 1622–1628.

Aqueous suspensions of methylcellulose have been evaluated as oral ultrasound contrast agents by Warren, P. S. et al. in *J. Chin Ultrasound* (1978) 6, pp. 315–320.

Microbubbles encapsulated with calcium alginate have recently been described as a potential ultrasound contrast agent by Wheatley, M. A. et al. in *Biomaterials* (1990) 11, pp. 713–717 and *Polymeric Materials Science and Engineering* (1990) 63, pp. 144–147.

A general disadvantage of existing particulate ultrasound contrast agents such as the sugar-based agents discussed above is their relative lack of stability in vivo. This is a particular problem in applications such as echocardiography, where there is a need for improved contrast agents combining sufficient stability and small microbubble size (typically less than about 10 μm, preferably less than about 7 μm) to permit passage through the pulmonary capillary bed and so allow enhanced visualisation of the left side of the heart, preferably for more than one passage of circulation.

The present invention is based on our finding that the in vivo stability and/or the echogenicity of microparticulate ultrasound contrast agents may be substantially enhanced by covalently modifying the structure of the microparticulate matrix, for example to introduce stabilising crosslinking groups or a lipophilic coating. The covalently bound stabilising moieties may furthermore be chosen to include biodegradable linkages, so that the contrast agents exhibit the important property of being rapidly eliminatable from the subject in a short term after use, e.g. preferably having a half life of not more than 48 hours in vivo, for example 1–12 hours.

BRIEF DESCRIPTION OF THE DRAWINGS

FIG. 1 shows the acoustic transmission for the exemplified products plotted against time.

Thus, according to one aspect of the present invention, there are provided ultrasound contrast agents in the form of microparticles comprising a biotolerable matrix in association with a gas or a precursor therefore, characterised in that the microparticles are stabilised by covalent bonding of the matrix.

It will be appreciated that the material of the biotolerable matrix must carry appropriate functional groups capable of reacting covalently with, for example, reagents such as crosslinking agents (including so-called zero-crosslinking agents) and/or reactive derivatives of lipids, e.g. as described in greater detail hereinafter. Subject to this requirement a wide range of biotolerable materials may be used in accordance with the invention, examples including carbohydrates (for example hexoses such as glucose, fructose or galactose: disaccharides such as sucrose, lactose or maltose; pentoses such as arabinose, xylose or ribose; α-, β- and γ- cyclodextrins; polysaccharides such as starch, hydroxyethyl starch, hydroxypropyl starch, amylose, amylopectin, glycogen, inulin, pulullan, dextran, carboxymethyl dextran, dextran phosphate, ketodextran or an alginate; and carbohydrates containing amino or amido groups, such as aminoethyldextran, chitin, chitosan, hyaluronic acid or heparin—the term "carbohydrate" as used herein is also intended to embrace sugar alcohols, e.g. alditols such as mannitol or sorbitol); imaging agents (for example X-ray contrast agents such as any of the commercially available carboxylic acid and non-ionic amide X-ray contrast agents typically containing at least one 2,4, 6-triiodophenyl group having at the 3- and/or 5-positions substituents such as carboxyl, carbamoyl, N-alkylcarbamoyl, N-hydroxyalkylcarbamoyl, acylamino, N-alkylacylamino or acylaminomethyl, as in metrizoic acid, diatrizoic acid, iothalamic acid, ioxaglic acid, iohexol, iopentol, iopamidol, iodixanol, iopromide, metrizamide, iodipamide, meglumine iodipamide, meglumine acetrizoate or meglumine diatrizoate); and polypeptides and proteins (e.g. gelatin or albumin such as human serum albumin).

Examples of contrast agents according to the invention include suspensions and solutions of biotolerable microparticles which have gas present as an inclusion in the voids of their crystal structure and/or adhered to their surface; and microbubbles encapsulated by biotolerable materials, for example insoluble polysaccharides such as calcium alginate.

In one embodiment of the invention the microparticulate biotolerable matrix is presented in the form of aggregates (for example having an aggregate size of 20–125 micrometres, such as 30–50 micrometres) of particles having a particle size of, for example, 1–50 micrometres, such as 5–10 micrometres. Such aggregates, which may be prepared by, for example, conventional micronisation techniques such as grinding or milling, e.g. by ball-milling, will tend to contain a substantial volume of air adsorbed on their surfaces and entrained in voids such as interparticle cavities or at grain boundaries between the crystallites. The particle size may, for example, be selected to be substantially commensurate with the desired microbubble size. In applications such as echocardiography this will typically be less than about 10 micrometres to permit passage through the pulmonary capillary bed and so allow enhanced ultrasound visualisation of the left side of the heart, preferably for more than one passage of circulation.

Stabilisation in accordance with the invention may, for example, be effected by covalently crosslinking the biotolerable matrix, before, during or after inclusion of any gas or gas precursor, using a crosslinking agent having at least two functional groupings able to react with functional groupings present in the biotolerable matrix. Numerous such pairs of interacting functional groups are known in the art, e.g. as described by Beaumert et al. in "Crosslinking techniques" (Meth. Enzymol. 172 (1989), pp. 584–609) or in the Pierce Handbook and General Catalogue (1989), pp. 284–311.

Thus, for example, hydroxyl groups in biotolerable matrices such as carbohydrates may be crosslinked as described in "Advances in Carbohydrate Chemistry and Biochemistry" ed. by R. Stuart Tipson and D. Horton, (1976) vol. 33, pp. 11–109 (Academic Press, New York). Examples of appropriate functional groupings for this purpose include halogen atoms such as chlorine or bromine, e.g. in the form of acyl halides such as alkanoyl or sulphonyl halides; sulphonate ester groups, e.g. alkyl sulphonate esters such as mesyloxy groups and aromatic sulphonate esters such as tosyloxy groups; α-halomethyl ester and keto groups; activated carboxyl groups, e.g. symmetrical or mixed anhydrides; activated hydroxyl groups; activated alkenes, e.g. α,β-unsaturated ketones, amides and esters, e.g. acrylate and methacrylate esters; conjugated diyne and enyne systems; epoxy groups; and acetal-forming aldehyde and ketone groups and derivatives thereof such as enol ethers or acetal or ketal groups. Examples of crosslinking agents useful for stabilising carbohydrate matrices include epichlorohydrin (e.g. as described by Kartha, K. P. R. et al. in *Staerke* (1985) 37, pp. 297–306) and other epoxide derivatives (e.g. as described in U.S. Pat. No. 4,126,669) and sodium trimetaphosphate (e.g. as described in WO 89/03674).

Biotolerable matrices containing carboxyl groups may, for example, be crosslinked by reaction with functional groups such as hydroxyl, mercapto, amino or diazo.

Crosslinking agents for use with proteinaceous or other biotolerable amino group-containing matrices include, for example, aldehydes, compounds containing activated carboxyl groups such as N-hydroxysuccinimidyl, imidoesters, nitroaryl halides, compounds containing nitrene precursor groups such as phenylazido, carbene percursors (e.g. diazo compounds and diazirines), ketones, isocyanates, isothiocyanates, semicarbazides and thiosemicarbazides, epoxides, phenol esters (e.g. nitrophenol esters), acyl azides and hydrazines, haloformates, and acyl halides (e.g. alkanoyl chlorides or sulphonyl chlorides such as mesyl or tosyl chloride). Dialdehydes are a preferred class of crosslinking agent for use with proteinaceous matrices.

Sulfhydryl groups may, for example, be reacted with functional groups such as maleimides, sulphonated maleimides, α-halomethyl carbonyl derivatives (e.g. esters, amides or ketones), alkyl or aralkyl halides, nitrosoureas, s-triazines, aziridines and pyridyl disulphides.

As indicated above, zero-crosslinking agents may also be employed. Thus, for example, aminoacid-containing substrates may be treated with condensing agents (e.g. a carbodiimide such as dicyclohexyl carbodiimide) to promote intramolecular reaction of the carboxyl and amino groups to form amide groups.

Crosslinking agents may be chosen so as to contain or form with the biotolerable matrix one or more biodegradable bonds having an appropriate degree of stability, particularly in cases where the matrix itself is not readily biodegradable. Suitable biodegradable linkages include, for example, amide, imide, imine, ester, anhydride, acetal, carbamate, carbonate, carbonate ester and disulphide groups. At least one such group may advantageously be present in the crosslinking grouping. In general, any esters will be biodegradable, particularly those containing the grouping —CO.O— or —O.CO.O—.

One particularly useful class of biodegradable ester groupings, which exhibits hydrolytic stability comparable to a traditional aliphatic ester but is highly cleavable enzymically in vivo has the structure

[in which each X, which may be the same or different, is selected from —O—, —S— and —NR—, where R represents a hydrogen atom or an organic group; each Y, which may be the same or different, represents carbonyl, thiocarbonyl, sulphonyl or phosphoryl (i.e. a group of formula

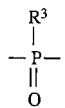

where $R^3$ is a hydrogen atom or an organic group) or a similar acid-forming group; each Z, which may be the same or different, is selected from —O—, —S— and —NR—, where R represents a hydrogen atom or an organic group; m and n, which may be the same or different, are each zero or 1; and $R^1$ and $R^2$, which may be the same or different, are each selected from hydrogen atoms, monovalent organic groups and groups of formula —X.Y.(Z)m— as hereinbefore defined, or $R^1$ and $R^2$ together form a divalent group].

Organic groups represented by R, R, $R^2$ and $R^3$ may, for example, each be a hydrocarbyl or heterocyclic group, for example having 1–20 carbon atoms, e.g. an aliphatic group such as an alkyl or alkenyl group (preferably having up to 10 carbon atoms), a cycloalkyl group (preferably having up to 10 carbon atoms), an araliphatic group such as an aralkyl group (preferably having up to 20 carbon atoms), an aryl group (preferably having up to 20 carbon atoms) or a heterocyclic group having up to 20 carbon atoms and one or more heteroatoms selected from O, S and N; such a hydrocarbyl or heterocyclic grouping may carry one or more substituents such as halogen atoms or groups of the formulae —$NR^4R^5$, —$CONR^4R^5$, —$OR^6$, —$SR^6$ and —$COOR^7$ (where $R^4$ and $R^5$, which may be the same or different, are hydrogen atoms, acyl groups or hydrocarbyl groups as defined for R, $R^1$, $R^2$ and $R^3$; $R^6$ is a hydrogen atom or an acyl group or a group as defined for R, $R^1$, $R^2$ and $R^3$; and $R^7$ is a hydrogen atom or a group as defined for R, $R^1$, $R^2$ and $R^3$). Where $R^1$ and $R^2$ represent a divalent grouping, this may be an alkylene, alkenylene, alkylidene or alkenylidene group (preferably having up to 10 carbon atoms) which may carry one or more substituents as defined above. In general R, $R^1$, $R^2$ and $R^3$ are preferably H or small groups such as $C_{1-4}$ alkyl groups.

Aliphatic groups R, $R^1$, $R^2$ and $R^3$ may be straight or branched, saturated or unsaturated, and include, for example, alkyl and alkenyl groups such as methyl, ethyl, isopropyl, butyl and allyl. Araliphatic groups include (monocarbocyclic aryl) alkyl groups such as benzyl. Aryl groups include mono- and bi-cyclic groups such as phenyl, tolyl and naphthyl. Heterocyclic groups include 5- and 6-membered rings preferably containing a single heteroatom, such as furyl, thienyl and pyridyl.

Possible substituents in hydrocarbyl groups R,$R^1$, $R^2$ and $R^3$ include hydroxyl, etherified hydroxyl (e.g. $C_{1-5}$ alkoxy such as methoxy), esterified hydroxyl (e.g. $C_{1-6}$ acyloxy such as acetoxy), etherified thiol, N-($C_{1-6}$ alkyl)amino, N-($C_{1-6}$ acyl)amino, N-($C_{1-6}$ acyl)-N-($C_{1-6}$ alkyl)amino, carbamoyl, N-($C_{1-6}$ alkyl) carbamoyl and halogen. Aromatic rings may carry $C_{1-6}$ alkyl groups, e.g. as in tolyl groups. Substituents may be present in combination and thus, for example, N-acyl and N-alkyl groups may carry hydroxyl or etherified or esterified hydroxyl groups.

Suitable crosslinking agents for stabilising biotolerable matrices in accordance with the invention include compounds of the formula

where M is a crosslinking divalent grouping and the groups A and B, which may be the same or different, optionally in conjunction with the groups to which they are attached, are functional groupings reactive with the biotolerable matrix, e.g. as hereinbefore described.

The group M may carry further groups reactive with the matrix to provide an even greater degree of crosslinking.

Preferably, the group M should not have a chain length of more than 50, more preferably not more than 30 atoms, and may, for example, be an alkylene or alkenylene group (e.g. containing up to 30, for example up to 10 carbon atoms, such as methylene or ethylene), a cycloalkylene group (e.g. containing up to 30, for example up to 10 carbon atoms), an arylene group (e.g. containing up to 30, for example up to 30 for example up to 20, carbon atoms), an aralkylene group (e.g. containing up to 20 carbon atoms) or a heterocyclic group (e.g. containing up to 30, for example up to 30, for example up to 20 carbon atoms and at least one heteroatom selected from O, N and S).

Biodegradable groups M may, for example, be of the form

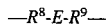

where $R^8$ and $R^9$, which may be the same or different represent divalent organic groups optionally interrupted by one or more heteroatoms and/or carrying one or more substituents containing such heteroatoms (e.g. carrying groups reactive with the matrix and/or further inert groups), and the group E is an ester grouping, for example of the formula —O.CO—, or —O.CO.O—, or adiester or diamide group of formula (I) as defined above. One useful class of crosslinking agents may be represented by the formula

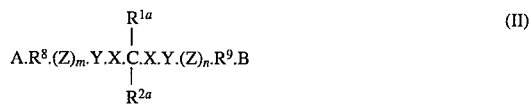

(wherein A,B,$R^8$,$R^9$,X,Y,Z,m and n are as hereinbefore defined; $R^{1a}$ and $R^{2a}$ are as defined for $R^1$ and $R^2$ except that they may represent groups —X.Y.(Z)$_m$.$R^8$.A or —X.Y.(Z)$_n$.$R^9$.B rather than groups —X.Y.(Z)$_m$—. A second useful class of crosslinking agents may be represented by the formula

(wherein X,Y,Z, m, $R^{1a}$, $R^{2a}$, $R^8$ and A have the above-defined meanings and L is a leaving group). Such compounds may be reacted with compounds of the formula

(where X,Y,Z and n are as hereinbefore defined and $R^{10}$ represents a hydrogen atom or an organic group), or appropriate reactive derivatives thereof (e.g. alkali metal salts of compounds of formula (IV) which are acids), to generate a biodegradable linkage of formula (I).

It will be appreciated that $R^{10}$ may represent an organic group such that, for example, the compound (III) reacts to form a compound of formula (II) or a precursor therefore. Alternatively the group R may represent a substrate which is to be crosslinked; in addition to the -(Z)$_n$.Y.X.H substituent or reactive derivative thereof such a substrate will also possess a functional grouping reactive with -A or -$R^8$A in formula (III).

The divalent organic groups $R^8$ and $R^9$ in the above formulae may, for example, be selected from alkylene and alkenylene groups (e.g. containing up to 20, more preferably up to 10 carbon atoms), cycloalkylene groups (preferably having up to 10 carbon atoms), arylene groups (containing one or more aromatic rings and preferably having up to 20 carbon atoms), aralkylene groups (preferably having up to 20 carbon atoms and which may be bonded via the aryl and/or alkyl moieties —such aralkylene groups include, for example, two aryl groups joined by an alkylene chain), and heterocyclic groups (having one or more heteroatoms preferably selected from O, N and S and preferably having up to 20 carbon atoms). The groups may carry substituents, e.g. as set out above for R, $R^1$, $R^2$ and $R^3$ and/or substituents such as oxo or thio groups. The carbon chains may be interrupted by heteroatoms such as O, N, S or P, e.g. in conjunction with oxo substituents to form linkages such as ester, thioester or amide groups. The presence of disulphide linkages may also be advantageous by virtue of their inherent bi-odearadability.

It will be appreciated that groups $R^8$ and/or $R^9$ may be chosen so as to include one or more further groups of formula (I) and that the grouping—$R^8$.A in formula (III) may be such that it terminates in a grouping

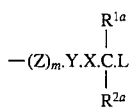

(where X, Y, Z, m, $R^{1a}$, $R^{2a}$ and L are as hereinbefore defined) capable of generating a biodegradable linkage of formula (I).

Leaving groups L in compounds of formula (III) include halogen atoms such as chlorine or bromine and sulphonyloxy groups such as mesyloxy or tosyloxy.

Crosslinking agents of formulae (II) and (III) may be prepared by any convenient method. Thus, for example, one or two moles of a compound of formula $$A.R^8.(Z)_m.Y.X.H \qquad (V)$$

(where X, Y, Z, m, $R^8$ and A are as hereinbefore defined, subject, if necessary and/or desired to A and any other reactive groups being protected), or a functional derivative thereof (e.g. a salt, for example an alkali metal salt such as the potassium or cesium salt of a compound (V) which is an acid), may be reacted with one mole of a compound of formula

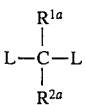

(where $R^{1a}$, $R^{2a}$ and L are as hereinbefore defined) to yield compounds of formula (III) and symmetrical compounds of formula (II) respectively. Alternatively, if an unsymmetrical compound of formula (II) is required, one may, for example, react equimolar quantities of a compound of formula (V), or a functional derivative thereof, and a compound of formula

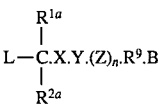

(where X, Y, Z, n, $R^{1a}$, $R^{2a}$, $R^9$, B and L are as hereinbefore defined, subject if necessary and/or desired to B and any other reactive groups being protected). Such reactions will normally be carried out in solution, for example in a polar solvent such as dimethylformamide.

Symmetrical compounds of formula (II) in which $R^{2a}$ represents a hydrogen atom, m and n are zero, each Y represents a carbonyl group and each X represents —O— may also be prepared by reacting a compound of formula $$A.R^8.CO.OH \qquad (VIII)$$

(where A and $R^a$ are as hereinbefore defined, subject, if necessary and/or desired to A and any other reactive groups being protected) with an aldehyde of formula $$R^{1a}.CHO \qquad (IX)$$

(where $R^{1a}$ is as hereinbefore defined) in the presence of an acid catalyst such as hydrochloric acid; if desired water may be removed from the reaction mixture by azeotropic distillation.

Compounds of formula (III) in which L is a halogen atom may also be prepared by reaction of a compound of formula (V) as hereinbefore defined, particularly such a compound in which Y represents a carbonyl group and X represents —O—, with an aryl thioether of formula

(where $R^{1a}$ and $R^{2a}$ are as hereinbefore defined and $R^{11}$ represents an aryl group such as phenyl), e.g. in a polar solvent such as dimethylformamide in the presence of a base such as pyridine, to yield a compound of formula

(wherein all the symbols are as hereinbefore defined) and halogenating this thioether, e.g. by reaction with sulfuryl chloride in a solvent such as dichloromethane or with bromine in a solvent such as carbon tetrachloride, to yield a compound (III) in which L is chlorine or bromine respectively.

Alternatively, compounds of formula (III) may be prepared by reaction of a compound of formula (V), as hereinbefore defined, with a chlorosulphate of formula

(wherein $R^{1a}$, $R^{2a}$, and L are as hereinbefore defined, L preferably being chlorine), e.g. using the method of Binderup et al. described in Synth. Comm. 14(9) (1984), pp. 857–864.

Protecting groups used in connection with A and B and any other reactive groups present may, for example, be those conventional in the art. Thus, for example, carboxyl groups may be protected using reductively cleavable ester groups such as benzyl, and hydroxyl groups may be protected using acid cleavable etherifying groups such as triphenylmethyl.

One may also prepare compounds of formulae (II) and (III) containing precursors for the A.$R^8$- (and/or -$R^9$.B groups where appropriate) and subsequently convert such precursor groups to the desired reactive groupings. Thus, for example, compounds in which A and/or B represent epoxide groups may be prepared by oxidation of precursors containing appropriately positioned (e.g. terminal) ethylenically unsaturated bonds (e.g. using a oxidising agent such as metachloroperbenzoic acid), or by reacting compounds containing appropriately positioned hydroxyl groups (e.g. phenolic hydroxyl groups) with reagents such as epichlorohydrin; compounds in which A.$R^8$- and/or -$R^8$.B represent enol ether groups may be prepared by, for example, acid-catalysed elimination from corresponding acetals or ketals. Hydroxyl group-containing precursors may also be activated by, for example, reaction with sulphonyl halides such as mesyl or tosyl chloride to generate reactive leaving groups such as mesylate or tosylate or with α,β-unsaturated alkenoyl halides such as acryloyl chloride to generate α,β-unsaturated esters.

Compounds of formula (VII) in which L represents a halogen atom may, for example, be prepared by reacting compounds of formulae

and

(where Hal represents a halogen atom and the remaining symbols have the above-defined meanings), e.g. in the presence of a base such as pyridine.

The preparation of a range of crosslinking agents of formulae (II) and (III) is described in greater detail in our International Patent Application No. PCT/EP92/00717, the contents of which are incorporated herein by reference.

In a further embodiment of the invention the ultrasound contrast agents have lipophilic groups and/or molecules covalently attached to the biotolerable matrix, if desired in the form of a coating. Thus, for example, lipids may be covalently attached to products such as gas-containing particles of carbohydrates such as galactose, galactosestarch mixtures or xylose or X-ray contrast agents such as iohexol, iodixanol or metrizamide so as to increase their stability in a controllable manner, e.g. by decreasing their solubility.

Lipids useful for this purpose include derivatives of fatty acids (e.g. long chain alkanoic or alkenoic acids preferably containing 10–50, e.g. 10–30 carbon atoms, such as capric, palmitic, stearic, linolenic, behenic, docosanedioic or melissic acid), aralkanoic acids (e.g. phenyl lower alkanoic acids such as 2-phenylbutyric acid), cholesterol derivatives (e.g. cholanic acids such as 5β-cholanic acid), and other biocompatible lipids possessing one or more functional groups, such as acid halide or anhydride groups or activated alkene groups covalently attachable to substituents such as hydroxyl groups. Thus, for example, surfactants such as poloxamers ("Pluronics") may be esterified to introduce an α,β-unsaturated lower alkenoyl group such as an acryloyl group which will covalently react with hydroxyl groups present in biotolerable matrices such as carbohydrates.

The lipophilic groups and/or molecules may be such as also to act as crosslinking agents; such groups may be introduced by, for example, reaction with appropriate bi-or poly-functional lipid derivatives.

In addition to or alternatively to air, any biocompatible gas may be employed in the contrast agents of the invention, for example nitrogen, oxygen, hydrogen, nitrous oxide, carbon dioxide, helium, argon, sulphur hexafluoride and low molecular weight optionally fluorinated hydrocarbons such as methane, acetylene or carbon tetrafluoride. The term "gas" as used herein includes any substance in the gaseous form at 37° C. The gas may be contained in the contrast agent in such a way that before use the product is non-contrast giving but becomes effective on administration, e.g. as a result of the gas forming microbubbles as a soluble matrix dissolves. The rate of microbubble formation may thus be controlled by, for example, selection of an appropriate degree of crosslinking or lipid attachment.

Gas precursors useful in contrast agents according to the invention include carbonates and bicarbonates (e.g. sodium or ammonium bicarbonate) and aminomalonate esters.

For applications in echocardiography, in order to permit free passage through the pulmonary system and to achieve resonance with the preferred imaging frequency of about 0.1–15 MHz, it may be convenient to employ microbubbles and microparticles having an average size of 0.1–10 μm, e.g. 1–7 μm; the use of microparticles of average size 1–2 μm to generate microbubbles with an average size of 4–7 μm is generally advantageous. Substantially larger bubbles and particles, e.g. with average sizes of up to 500 μm, may however be useful in other applications, for example gastrointestinal imaging.

The following non-limitative Examples serve to illustrate the invention:

Preparation 1 Milled D-(+)-Galactose 20 g of commercially available D-(+)-galactose (Reinst ph. Ned. Merck) was ball-milled in an aluminium ball-mill with 3×1.5 cm diameter aluminium balls for two hours. The resulting powder mixture consisted of crystals and aggregates of galactose in the particle size range of 1–100 μm (measured by light scattering, Malvern Mastersizer).

Preparation 2 Milled D-(+)-Galactose/Starch 5 g of commercially available D-(+)-galactose, (Reinst Ph. Ned, Merck) was mixed with 5 g of commercially available starch (Reppal PSM 70, Reppe glykos, Sweden) and ground in a stainless steel ball mill (Retsch centrifugal ball mill, S 1) with a 50 ml grinding cup and 3×20 mm balls for 10 minutes.

Preparation 3 Milled Xylose 10 g of commercially available D-(+)-xylose (BHD) was ground in a stainless steel ball mill with a 50 ml grinding cup and 3×20 mm balls for 10 minutes.

Preparation 4 Palmitic Acid Carbonic Acid Monoisobutyl Ester Mixed Anhydride

Palmitic acid (5.0 g, 19.5 mmol) was suspended in dry acetonitrile with triethylamine (1.97 g, 19.5 mmol) under nitrogen. The suspension became a thick slurry after stirring for 1 hour. Isobutyl chloroformate (2.66 g, 19.5 mmol) was added in one portion while cooling in an icewater bath. After 30 min., the reaction was stirred overnight at room temperature. The resulting suspension was filtered, and the pink filtrate was evaporated to dryness at 30° C., yielding 7.8 g of a pink/white solid. $^{13}$C-NMR confirmed the structure of the mixed anhydride.

Preparation 5 5-β-Cholanic Acid Carbonic Acid Monoisobutylester Mixed Anhydride

5-β-Cholanic acid (Sigma, 3.6 g, 10 mmol), was dissolved in diethyl ether (100 ml). Triethylamine (1.38 ml, 10 mmol) was added, and the reaction mixture was cooled to 0° C. Isobutyl chloroformate (1.37 g, 10 mmol) was added dropwise with vigorous stirring over 2 minutes. After a voluminous precipitation, diethyl ether (100 ml) was added. Stirring was continued at 0° for 40 minutes; the icebath was removed and stirring was continued for another 60 minutes.

The precipitate was removed by filtration and the filtrate was transferred to an extraction funnel and extracted with saturated sodium bicarbonate (25 ml) and water (2×25 ml)

and dried over MgSO$_4$. The solvent was removed in vacuo, giving an 80% yield of a semisolid waxy substance. The product was characterised by 13C-NMR: CO-acid:168.37 ppm, CO-carbonate:149.36 ppm.

Preparation 6 Melissic Acid Carbonic Acid Monoisobutyl Ester Mixed Anhydride Melissic acid (Sigma, 0.5 g, 1.1 mmol) was dissolved in diethyl ether (25 ml). Triethylamine (151 µl, 1.1 mmol) was added, and the reaction mixture was cooled to 0° C. Isobutyl chloroformate (151 µl, 1.1 mmol) was added dropwise with vigorous stirring over 2 minutes. The reaction mixture was treated as described in Preparation 5, and the product was characterised by $^{13}$C-NMR:CO-acid:168.596 ppm, CO-carbonate:149.728 ppm.

Preparation 7 Docosanedioic Acid Bis(Carbonic Acid Monoisobutyl Ester Mixed Anhydride)

Docosanedioic acid (Fluka, 1 g, 2.7 mmol), was dissolved in diethyl ether (25 ml). Triethylamine (747 µl, 2.7 mmol) was added and the reaction mixture was cooled to 0° C. Isobutyl chloroformate (7431 µl, 2.7 mmol) was added dropwise with vigorous stirring over 2 minutes. The reaction mixture was treated as described in Preparation 5, and the product was characterised by $^{13}$C-NMR: CO-acid:168.049 ppm, CO-carbonate: 149.359 ppm.

Preparation 8 Bisacryloylpluronic F68

Pluronic F68 (Fluka, 8.35 g, 1 mmol) was dissolved in toluene (50 ml) and heated to 50° C. under nitrogen. Triethylamine (1.4 ml, 10 mmol) was added. Acryloyl chloride (Fluka, 0.94 g, 10 mmol) in toluene (10 ml) was added over 10 minutes with stirring. Stirring was continued at 50° C.; monitoring by TLC indicated full consumption of the starting material after 2 hours. The precipitate was removed by filtration and the filtrate was poured into diethyl ether (750 ml) with vigorous stirring. The precipitate was collected by filtration, redissolved in toluene (30 ml) with heating and added dropwise to a 1:1 mixture of diethyl ether and pentane (500 ml) with vigorous stirring. The resulting mixture was stored in a refrigerator overnight, whereafter the precipitated product was collected by filtration and dried under vacuum. Yield: 7 g. The product was characterized by FT-IR:CO- 1724 cm$^{-1}$, disappearance of OH—at 3500 cm$^{-1}$.

EXAMPLE 1

Milled D-(+)-Galactose Covalently Bonded To Palmitic Acid

A sealable 25 ml flask was loaded with 1.00 g of milled galactose prepared as described in Preparation 1 under nitrogen and to the flask was added 6 mg of palmitic acid carbonic acid monoisobutyl ester mixed anhydride prepared as described in Preparation 4 dissolved in 10 ml dry methylene chloride under nitrogen. The sealed flask was shaken gently for 18 hours at ambient temperature. The solid content was isolated by filtration, washed several times with methylene chloride, and dried over calcium chloride in a desiccator at 50 mbar and ambient temperature for 24 hours. The resulting product was a white solid with the same appearance as the starting material. Weight: about 1 g.

EXAMPLES 2–21

The procedure of Example 1 was repeated using the acid derivatives listed in Table 1 in the amount shown.

TABLE 1

| Example No. | Acid derivative | Amount (% w/w relative to galactose) |
|---|---|---|
| 2 | Palmitic acid carbonic acid monoisobutyl ester mixed anhydride (Preparation 4) | 0.2 |
| 3 | Palmitic acid carbonic acid monoisobutyl ester mixed anhydride (Preparation 4) | 2 |
| 4 | Palmitic acid carbonic acid monoisobutyl ester mixed anhydride (Preparation 4) | 20 |
| 5 | 2-Phenylbutyric acid anhydride (Fluka) | 0.05 |
| 6 | 2-Phenylbutyric acid anhydride (Fluka) | 0.5 |
| 7 | Linolenic acid anhydride (Sigma) | 0.05 |
| 8 | Linolenic acid anhydride (Sigma) | 0.5 |
| 9 | Stearic acid anhydride (Sigma) | 0.05 |
| 10 | Stearic acid anhydride (Sigma) | 0.5 |
| 11 | Stearic acid anhydride (Sigma) | 5 |
| 12 | Capric acid anhydride (Sigma) | 0.05 |
| 13 | Capric acid anhydride (Sigma) | 0.5 |
| 14 | Behenic acid anhydride (Sigma) | 0.05 |
| 15 | Behenic acid anhydride (Sigma) | 0.5 |
| 16 | 5β-Cholanic acid carbonic acid monoisobutyl ester mixed anhydride (Preparation 5) | 0.1 |
| 17 | 5β-Cholanic acid carbonic acid monoisobutyl ester mixed anhydride (Preparation 5) | 1 |
| 18 | Melissic acid carbonic acid monoisobutyl ester mixed anhydride (Preparation 6) | 0.1 |
| 19 | Melissic acid carbonic acid monoisobutyl ester mixed anhydride (Preparation 6) | 0.2 |
| 20 | Melissic acid carbonic acid monoisobutyl ester mixed anhydride (Preparation 6) | 1 |
| 21 | Docosanedioic acid bis(carbonic acid monoisobutyl ester mixed anhydride) (Preparation 7) | 6 |

EXAMPLES 22–24

Milled D-(+)-galactose/starch (1:1) prepared as described in Preparation 2 was reacted with the materials shown in Table 2 in the stated quantities, using the procedure of Example 1.

TABLE 2

| Example No. | Acid derivative | Amount (% w/w relative to galactose) |
|---|---|---|
| 22 | Bis(acryloyl) pluronic F68 (Preparation 8) | 0.1 |

TABLE 2-continued

| Example No. | Acid derivative | Amount (% w/w relative to galactose) |
| --- | --- | --- |
| 23 | Bis(acryloyl) pluronic F68 (Preparation 8) | 1 |
| 24 | Behenic acid anhydride (Sigma) | 0.2 |

EXAMPLE 25

Milled xylose prepared as described in Preparation 3 was reacted with 0.2% ww of behenic acid anhydride (Sigma) using the procedure of Example 1.

EXAMPLE 26

Reaction of Dioleoylphosphatidylethanolamine (DOPE) with Milled D-(+)-Galactos

Milled D-(+)-galactose prepared as described in Preparation 1 (6.0 g) was suspended in dry acetone, and carbonyldiimidazole (Fluka, 7.32 g, 45.1 mmol) was added. After stirring for 30 minutes at ambient temperature, the solid was filtered off and washed with dry acetone (3×50 ml) on the filter. The solid was resuspended in dry methylene chloride (50 ml), and a solution of dioleoylphosphatidylethanolamine (provided by Hafslund Nycomed Pharma, Austria, 1.00 g, 1.43 mmol) in dry methylene chloride (30 ml) was added. The sealed reaction flask was shaken at ambient temperature for 72 hours. The solid was filtered off and washed on the filter with methylene chloride (3×50 ml). The slightly yellow solid (5.5 g) was kept in a desiccator over calcium chloride.

EXAMPLE 27

6-O-Palmitoyl-D-Galactoyranose (A) 6-O-Palmitoyl-1,2,3,4-diisopropylidene-D-galactopyranose 1,2,3,4-Diisopropylidene-D-galactopyranose (Sigma, 13.4 g, 51.3 mmol) and triethylamine (7.15 ml, 51.3 mmol) were dissolved in methylene chloride (150 ml) and cooled to 0° C. Palmitoyl chloride (Aldrich, 4.1 g, 51.3 mmol) dissolved in methylene chloride (100 ml) was added dropwise with stirring over 1 h. The cooling bath was removed and the reaction mixture was stirred overnight. The precipitate was removed by filtration, the filtrate was transferred to a separating funnel and extracted with water (3×50 ml), dried over $MgSO_4$ and the solvent was removed in vacuo. The residue was a light brownish oil which solidified to waxy crystals. Crude yield: 23 g. The crude product was used without further purification. A small aliquot was recrystallized for characterisation. FT-IR:CO-1734 $cm^{-1}$. $^{13}$C-NMR: CO-ester 172.79. Mp. 124°–127° C.

(B) 6-O-Palmitoyl-D-glactopyranose

6-O-Palmitoyl-D- 1,2,3,4-diisopropylidene-D-galactopyranose (6g) was dissolved in acetic acid (25 ml) and heated to 100° C. under nitrogen for 6h. During subsequent cooling to room temperature, the product precipitated from the solvent, and was left at room temperature overnight. The crystals were collected by filtration and dried under vacuum. Yield:3.3 g. The product was characterized by FT-IR:CO-1734 $cm^{-1}$; OH—3464 $cm^{-1}$.

EXAMPLE 28

6-O-Palmitoyl-D-Galacopyranose/Galactose Mixtures (A) D-(+)-galactose (2g) was dissolved in purified water (2.87g) and sterile filtered. 6-O-Palmitoyl-D-galactopyranose (0.25 g) prepared as described in Example 27 was dissolved in ethanol (3 g) and sterile filtered. The solution of the palmitoyl-galactopyranose was added to the galactose solution under stirring and the whole mixture was taken to dryness under vacuum (10 torr, 50° C.). The product was dried in a desiccator overnight.

(B) The procedure of (A) was repeated using 6-O-palmitoyl-D-galactopyranose (0.50g) dissolved in ethanol (6g).

EXAMPLE 29

Iohexol Functionalised with Palmitic Acid

A sealable 25 ml flask was loaded with 1.00 g of Iohexol (NYCOMED), ball-milled as described in Preparation 1, under nitrogen. To the flask was added 35 mg of palmitic acid carbonic acid monoisobutyl ester mixed anhydride (prepared as described in Preparation 4) dissolved in 10 ml dry methylene chloride under nitrogen, and the sealed flask was shaken gently for 18 hours at ambient temperature. The solid was isolated by filtration and washed several times with methylene chloride, and dried over calcium chloride in a desiccator at 50 mbar and ambient temperature for 24 hours. The resulting product was a white solid with the same appearance as the starting material. Weight: about 1 g. A sample of the product was added to water under a microscope, and a number of gas bubbles were observed.

EXAMPLE 30

Iodixanol Functionalised with Palmitic Acid 1.00 g of iodixanol, ball-milled as described in Preparation 1, was reacted with 12 mg of palmitic acid carbonic acid monoisobutyl ester mixed anhydride (prepared as described in Preparation 4) using the method of Example 29. About 1 g white solid with the same appearance as the starting material was recovered. As in Example 29, microscopy showed development of gas bubbles when the product was added to water.

EXAMPLE 31

Metrizamide Functionalised with Palmitic Acid 1.00 g of Amipaque, ball-milled as described in Preparation 1, was reacted with 15 mg of palmitic acid carbonic acid monoisobutyl ester. mixed anhydride (prepared as described in Preparation 4) using the method of Example 29. About 1 g white solid with the same appearance as the starting material was recovered. Microscopy showed development of a plurality of gas bubbles when the product was added to water.

EXAMPLE 32

D-(+)-Galactose Crosslinked with Methylene Diacrylate (A) Methylene Diacrlate

A solution of potassium hydroxide (1.00M, 40.00 ml) was added to acrylic acid (2.88 g, 40.00 mmol) at 0° C., and the solution was freeze dried for 16 h. Dry DMF (200 ml) was added and the suspension heated to 60° C. under a dry $N_2$ atmosphere. Diiodomethane (1.61 ml, 20.00 mmol) was added in two portions during 10 min., and the reaction mixture left for 4 days at 60° C. The solvent was removed under reduced pressure (0.05 mm Hg) and diethyl ether (140 ml), saturated aqueous sodium hydrogen carbonate (50 ml) and water (50 ml) were added. The aqueous layer was extracted with diethyl ether (6×60 ml), and the combined ether extracts washed with water (4×50 ml), dried ($MgSO_4$) and evaporated to give 1.06 g (34%) product. 1H-NMR (60 MHz, $CDCl_3$): 5.81–6.61 (2×$CH_2$=CH-$_1$m), 5.84 ($CH_2$, s).

B) Milled D-(+)-Galactose Crosslinked with Methylene Diacrylate

A sealable 25 ml flask was loaded with 1.00 g of milled D-(+)-galactose prepared as described in Preparation 1 under nitrogen and to the flask was added methylene diacrylate (500 mg) dissolved in dry methylene chloride (10 ml) under nitrogen. The sealed flask was shaken gently for 18 hours at ambient temperature. The solid content was isolated by filtration and washed several times with methylene chloride, and dried over calcium chloride in a dessicator at 5 mbar and ambient temperature for 24 hours. The resulting product was a white solid with the same appearance at the starting material. Weight: about 0.96 g.

EXAMPLE 33 D) Echogenicity in vitro 10 ml of propylene glycol mixed with 90 ml of 5% dextrose in water was used as a carrier liquid for determining the echogenicity of products of the Examples. 1.0 g of each product to be tested was dispersed in 3.0 ml of the carrier liquid and shaken for 15 seconds. The resulting mixture as added to 52 ml of 5% human serum albumin infusion solution in the measurement cell and the acoustic effects of the products were investigated by measuring the acoustic transmission through the samples using a 5 MHz broadband transducer in a pulse-reflection technique. The temperature in the measurement cell was stabilised to 37° C. and circulation of the liquid was maintained by means of stirring at a constant rate. Ultrasound transmission through the samples was measured as a function of time over a duration of 390 seconds. Results were normalised to measurements on a reference consisting of 55 ml of 5% human serum albumin infusion solution.

Results for a number of the exemplified products and comparative results for unmodified milled D-(+)-galactose prepared as described in Preparation 1 are shown in the accompanying drawing. It will be apparent that the products of the invention exhibit a strong effect on ultrasonic attenuation in vitro, the effect persisting for several minutes.

We claim:

1. Ultrasound contrast agents in the form of microparticles comprising a biotolerable matrix in association with a gas or precursor therefore, the gas comprising $SF_6$ or a fluorinated low molecular weight hydrocarbon, in which the microparticles are stabilised by the presence of cross-linking groupings covalently attached to the matrix.

2. Ultrasound contrast agents as claimed in claim 1 in which the biotolerable matrix is a carbohydrate.

3. Ultrasound contrast agents as claimed in claim 2 in which the carbohydrate is galactose.

4. Ultrasound contrast agents as claimed in claim 1 in which the biotolerable matrix is an X-ray contrast agent.

5. Ultrasound contrast agents as claimed in claim 1 in which the microparticles are present in the form of aggregates having an aggregate size of 30–50 micrometres of microparticles having a particle size of 5–10 micrometres.

6. Ultrasound contrast agents as claimed in claim 5 in which the said aggregates have been prepared by ball-milling.

7. Ultrasound contrast agents as claimed in claim 1 in which the crosslinking groupings contain linkages which are biodegradable in vivo, and which are selected from the group consisting of amide, imide, imine, ester, anhydride, acetal, carbamate, carbonate, carbonate ester and disulphide groups.

8. Ultrasound contrast agents as claimed in claim 1 in which the crosslinking groups contain linkages which are biodegradable in vivo and are of the formula (I)

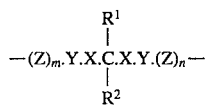

wherein each X, which may be the same or different, is selected from the group consisting of —O—, —S— and —NR—, where R represents a hydrogen atom or an organic group; each Y, which may be the same or different, represents carbonyl, thiocarbonyl, sulphonyl, phosphoryl or a similar acid-forming group; each Z, which may be the same or different, is selected from the group consisting of —O—, —S— and —NR—, where R is as defined above; m and n, which may be the same or different are each zero or 1, and $R^1$ and $R^2$, which may be the same or different, are each selected from the group consisting of hydrogen atoms, monovalent organic groups and groups of formula -X.Y.(Z)$_m$ as hereinbefore defined, or $R^1$ and $R^2$ together form a divalent organic group.

9. Ultrasound contrast agents as claimed in claim 7 in which the crosslinking groupings contain linkages which are biodegradable in vivo and which are of formula (Ia):

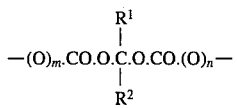

where m and n are each 0 or 1;

$R^1$ and $R^2$ are each selected from the group consisting of hydrogen atoms, monovalent organic groups and groups of formula —O.CO.(O)$_m$; or $R^1$ and $R^2$ together form a divalent organic group.

10. Ultrasound contrast agents as claimed in claim 1 wherein the hydrocarbon is perfluorinated.

11. Ultrasound contrast agents as claimed in claim 7 wherein the hydrocarbon is perfluorinated.

12. Ultrasound contrast agents as claimed in claim 8 wherein the hydrocarbon is perfluorinated.

13. Ultrasound contrast agents as claimed in claim 9 wherein the hydrocarbon is perfluorinated.

* * * * *